United States Patent [19]
Bunker

[11] Patent Number: 5,855,950
[45] Date of Patent: Jan. 5, 1999

[54] METHOD FOR GROWING AN ALUMINA SURFACE ON ORTHOPAEDIC IMPLANT COMPONENTS

[75] Inventor: Stephen N. Bunker, Wakefield, Mass.

[73] Assignee: Implant Sciences Corporation, Wakefield, Mass.

[21] Appl. No.: 777,411

[22] Filed: Dec. 30, 1996

[51] Int. Cl.[6] .............................. B05D 3/00; C23C 14/08; A61F 2/28
[52] U.S. Cl. .......................... 427/2.27; 427/529; 427/528; 427/526; 623/16
[58] Field of Search .................................. 427/226, 227, 427/529, 528, 526; 623/16

[56] References Cited

U.S. PATENT DOCUMENTS

| | | | |
|---|---|---|---|
| 3,925,187 | 12/1975 | Bernard | 427/529 |
| 4,021,326 | 5/1977 | Pollner et al. | 204/195 |
| 4,041,196 | 8/1977 | Baldi et al. | 427/252 |
| 4,263,681 | 4/1981 | Notton | 3/1.91 |
| 4,427,501 | 1/1984 | Rogers | 204/37 |
| 4,507,189 | 3/1985 | Doi et al. | 427/529 |
| 4,599,085 | 7/1986 | Riess et al. | 623/16 |
| 4,615,705 | 10/1986 | Scales et al. | 623/11 |
| 4,634,600 | 1/1987 | Shimizu et al. | 427/531 |
| 4,743,493 | 5/1988 | Sioshansi et al. | 428/217 |
| 4,790,851 | 12/1988 | Suire et al. | 427/2.26 |
| 4,822,369 | 4/1989 | Oueveau et al. | 623/22 |
| 4,847,163 | 7/1989 | Shimamune et al. | 427/227 |
| 4,855,026 | 8/1989 | Sioshansi | 204/192.11 |
| 4,876,984 | 10/1989 | Kinoshita et al. | 427/529 |
| 5,037,438 | 8/1991 | Davidson | 623/18 |
| 5,045,345 | 9/1991 | Singer | 623/18 |
| 5,123,924 | 6/1992 | Sioshansi | 623/16 |
| 5,133,757 | 7/1992 | Sionshansi | 623/18 |
| 5,205,921 | 4/1993 | Shirkanzadeh | 205/318 |
| 5,350,607 | 9/1994 | Tyson | 427/529 |
| 5,362,311 | 11/1994 | Amino et al. | 623/22 |
| 5,383,934 | 1/1995 | Armini et al. | 623/16 |
| 5,413,820 | 5/1995 | Hayashi | 427/529 |
| 5,618,575 | 4/1997 | Peter | 427/529 |

FOREIGN PATENT DOCUMENTS

| | | | |
|---|---|---|---|
| 3027472 | 2/1982 | Germany | 427/2.27 |
| 3342562 | 6/1985 | Germany | 623/22 |

OTHER PUBLICATIONS

Dillich, S.A., et al. "Friction and Wear Behavior of a Cobalt–Based Alloy Implanted with Ti or N" *Mat. Res. Soc. Symp. Proc.* vol. 27, (1984) pp. 637–642 no month.

Sioshansi, P., "Medical applications of Ion Beam Processes" *Nuclear Instruments and Methods in Physics Research* B19/20 (1987) 204–208.

Ogata, K., et al. "Properties of Aluminum Nitride Films by an Ion Beam and Vapor Deposition Method" *Nuclear Instruments and Methods in Physics Research* B39 (1989) 178–181 no month.

Williams, J.M. et al., "Ion Implantation of Surgical Ti–6A1–4V Alloy", Surface Modification of Metals by Ion Beams, Proceedings of the International Conference on Surface Modification of Metals by Ion Beams, pp. 237–248:1985. no month.

(List continued on next page.)

*Primary Examiner*—Marianne Padgett
*Attorney, Agent, or Firm*—Foley, Hoag & Eliot, LLP

[57] ABSTRACT

A method is disclosed for ion beam treating orthopaedic parts by ion implanting the parts with aluminum ions while the parts are immersed in an oxygen-containing background gas. When the parts are at sufficiently elevated temperature, a highly adherent layer of aluminum oxide is grown which provides a low friction, low wear articulating surface. The interface between the semi-pure aluminum oxide and the substrate orthopaedic part consists of a composition which gradually grades with depth between the grown aluminum oxide and the pure substrate material. This interface has a thickness dependent on the processing parameters, typically hundreds of Angstroms. In an alternative embodiment, the thickness of the alumina layer may be increased by simultaneously depositing aluminum oxide on the parts.

30 Claims, 2 Drawing Sheets

OTHER PUBLICATIONS

Dillich, S.A., et al., "Friction and Wear Behavior of a Cobalt–Based Alloy Implanted with Ti or N", Mat. Res. Soc. Symp. Proc. vol. 27, pp. 637–642 (1984). no month.

P. Sioshansi, "Medical Applications of Ion Beam Processes", Nuclear Instruments and Methods in Physics Research B19/20, pp. 204–208 (1987). no month.

Kumar, P., et al. "Low wear rate of UHMWPE against zirconia ceramic (Y–PSZ) in comparison to alumina ceramic and SUS 316L alloy" *Journal of Biomedical Materials Research,* vol. 25 (1991) 813–828, no month.

Iwaki, M., et al. "Surface modification of iron and steel by zirconium or yttrium ion implantation and their electrochemical properties" *Surface and Coatings technology,* 51 (1992) 1–5, no month.

Streicher, R.M., et al. Ceramics Surfaces as Wear Partners for Polyethylene, *Bioceramics,* vol. 4, ,(Sep. 1991).

Kumar, Praveen, et al. "Low wear rate of UHMWPE against zirconia ceramic (Y–PSZ) in comparison to alumina ceramic and SUS 316L alloy", Journal of Biomedical Materials Research, vol. 25, 813–828 (1991) no month.

R. Sizmann, "The Effect of Radiation Upon Diffusion in Metals", Journal of Nuclear Materials 69 & 70, pp. 386–412 (1968) no month.

R.M. Streicher et al., "Ceramic Surfaces as Wear Partners for Polyethylene" in *Bioceramics,* vol. 4, pp. 9–16 ed. by W. Bonfield (1991) no month.

E. Dorre, "Retrieval and Analysis of Ceramic Hip Joint Components", Society for Biomaterials, Symposium on Retrieval and Analysis of Surgical Implants and Biomaterials, Utah; Aug. 1988.

METHOD FOR GROWING AN ALUMINA SURFACE ON ORTHOPAEDIC IMPLANT COMPONENTS

TECHNICAL FIELD

The present invention relates to a method for ion treating orthopaedic implant components with aluminum and oxygen in order to grow a surface layer of aluminum oxide with a graded interface to the component's articulating surface.

BACKGROUND OF THE INVENTION

Orthopaedic components, in particular femoral hips and knees, are commonly manufactured from alloys of cobalt plus chromium, titanium, or stainless steel. Additionally, the ceramic materials aluminum oxide (alumina) and zirconium oxide (zirconia) are also used for femoral hips. The use of bulk ceramic materials is avoided in applications such as femoral knees, where the prosthesis is subject to tensile forces, since these materials are known to be weak under such conditions. There are numerous studies [see R. M. Streicher, "Ceramic Surfaces as Wear Partners for Polyethylene", in Bioceramics, London, ed. by W. Bonfield, G. W. Hastings, and K. E. Tanner, Butterworth-Heinemann, 1991, and E. Dörre, "Retrieval and Analysis of Ceramic Hip Joint Components", Trans. Soc. Biomat. 66, 1988] indicating that an alumina surface causes decreased wear on the companion ultra high molecular weight polyethylene (UHMWPE) articulating surface compared to a metal alloy femoral component. See also U.S. Pat. No. 5,037,438, J. Davidson and "Low Wear Rate of UHMWPE Against Zirconia Ceramic (Y-PSZ) in Comparison to Alumina Ceramic and SS316L Alloy", J. of Biomed. Mat. Res. 25, p. 813 (1991).

There exist numerous well-known methods for depositing a coating of alumina on an arbitrary surface, such as evaporation, sputtering, arc deposition, laser deposition, and chemical vapor deposition. Such techniques are characterized by an abrupt discontinuity in composition and properties across the interface between substrate and coating. Such discontinuity often causes poor adhesion or interfacial stress leading to debonding of the coating. The articulating surfaces of orthopaedic appliances, which are required to function without repair for periods in excess of ten years, rarely are provided with such coatings, mainly due to the risk of debonding or flaking. The flakes or particles are often trapped in the UHMWPE, resulting in a more rapid 3-body wear which further produces even more particles.

The use of high energy ion implantation of various elements is well known for improving the surface properties of metals, particularly decreasing wear and friction. See "Surface Modification of Metals by Ion Beams", Elsevier Sequoia (1984). For alloys containing primarily the elements cobalt and chromium, ion implanted titanium and nitrogen have been successfully employed. See "Friction and Wear Behavior of Cobalt-Based Alloy Implanted with Ti or N", Mat. Res. Soc. Symp. Proc. 27, p. 637 (1984). Similarly for orthopaedic components, see "Medical Applications of Ion Beam Processes", Nuc. Inst. and Meth. in Physics Res. B19/20, p. 204–208 (1987) and U.S. Pat. No. 5,123,924, Sioshansi et al.

Ion implantation is useful as a treatment for femoral orthopaedic components because the ions are imbedded throughout a zone below the surface of the component rather than being deposited onto the surface, thus avoiding the adhesion problem of a discontinuity at an interface. However, ion implantation is normally unable to create a surface layer of useful thickness or in arbitrary molecular form. The lack of surface layers is primarily caused by sputtering, which erodes the treated surface. After a sufficient dose is implanted, the rate of sputter erosion of substrate plus previously implanted atoms becomes equal to the rate of addition of atoms, thus determining a maximum possible concentration of implanted atoms. Even if the rate of sputtering happens to be sufficiently small, thus enabling a sufficient quantity of atoms to be retained, the atoms are unlikely to be in a desired molecular form such as a ceramic, but rather as individual atoms in a mixture or alloy. A method for avoiding these problems for the specific case of zirconia has been described. See U.S. Pat. No. 5,383,934, Armini et al. An alternate method for improving the adhesion of alumina coatings on substrates has also been given. See U.S. Pat. No. 5,045,345, Singer.

SUMMARY OF THE INVENTION

It is therefore an object of this invention to provide a method for growing a surface layer of aluminum oxide on orthopaedic prostheses.

It is a further object of this invention to provide such a method for growing aluminum oxide on femoral hip ball and knee orthopaedic prostheses made from an alloy primarily consisting of cobalt and chromium.

It is a further object of this invention to provide such a method for creating orthopaedic prostheses with a very low coefficient of friction on the articulating surface.

It is a further object of this invention to provide such a method for creating orthopaedic prostheses having a longer useful life.

This invention results from the realization that aluminum atoms diffuse sufficiently rapidly in alloys consisting primarily of cobalt and chromium at temperatures that do not significantly alter the relevant properties of the alloy. This invention further results from the realization that the rate of aluminum or oxygen diffusion through the several materials and compositions present is enhanced by the bombarding aluminum ion implantation beam, an effect known as ion assisted diffusion. See R. Sizmann, "Radiation Enhanced Diffusion", J. Nucl. Mater. 69/70, 386 (1968). This invention further results from the realization that a low partial pressure of oxygen-containing gas can provide the source for the oxygen diffusion. This invention further results from the realization that the diffusing oxygen will preferentially react with the aluminum to form aluminum oxide. This invention further results from the realization that free aluminum atoms which diffuse outward to the surface of the orthopaedic prosthesis will react with the low partial pressure of oxygen-containing gas to form aluminum oxide as a grown surface layer in addition to the aluminum oxide also formed sub-surface by inward oxygen diffusion. This invention further results from the realization that the aluminum oxide formed sub-surface provides a graded interfacial composition between pure aluminum oxide and pure cobalt-chromium alloy.

No measured data on the diffusion rate of aluminum in either bulk cobalt or chromium have been found. The diffusion rate constants of aluminum and oxygen in aluminum oxide (oxygen in polycrystalline aluminum oxide) have been measured as ($D_o$=21.5 cm$^2$/sec, $E_o$=4.8 eV) and ($D_o$= 5.2 cm$^2$/sec, $E_o$=4.9 eV), respectively. These constants can be used to predict the rate of diffusion of atoms as a function of temperature using the relationship $D=D_o e^{-E_o/kT}$ cm$^2$/sec. An approximate measure of the typical distance diffused when heat is applied for a known time t is given by $\sqrt{(DT)}$ cm. The predicted diffusion distance of either aluminum or oxygen in pure aluminum oxide is very small at a temperature between 400° and 650° C. (less than 1 Angstrom in either case). In order to permit processing the component in a reasonable period of time given a typical useful coating thickness of 5 micrometers, the diffusion constant should be greater than $10^{-16}$ cm$^2$/sec. The method taught by Singer in U.S. Pat. No. 5,045,345 utilizes a highly elevated temperature to produce diffusion (greater than 660° C. required and in Example 2, 850° C. actually used). Such a high temperature process is incompatible with substrates that can be thermally modified under such extreme conditions.

The low rate of diffusion of aluminum or oxygen in aluminum oxide can be avoided by allowing the diffusion to occur during high energy ion bombardment. Radiation- or ion-enhanced diffusion can occur aided by metastable defects produced by beam-induced atomic displacements, thus greatly enhancing the flux of oxygen atoms that may be usefully transported into the component. This enhanced flux is considerably more than possible at a given component temperature without ion bombardment even if the ambient partial pressure of oxygen-containing gas is only $1 \times 10^{-5}$ Torr. Singer teaches the use of an ambient pressure of 760 Torr (one atmosphere), nearly 8 orders of magnitude greater. Ion enhanced diffusion allows a significant diffusion of both oxygen and aluminum to occur at a component temperature of only 400° C.

In practice, it is found that the instantaneous rate of ion bombardment needed to enhance the atomic diffusion is over 10 microamperes/cm$^2$ and preferably at least 25 microamperes/cm$^2$. The effect increases with increasing rate, thus lowering the required ambient temperature.

Additionally, because the diffusion is sufficiently rapid, it is possible to diffuse the ion implanted aluminum atoms through any intervening aluminum oxide near to the external surface, where the outward-diffusing aluminum atoms may combine advantageously with inward-diffusing oxygen to grow a layer of nearly pure aluminum oxide coincidentally during the ion implantation step. The thickness of the grown layer of aluminum oxide is related to the temperature, total dose of aluminum atoms, dose rate, and ambient partial pressure of oxygen-containing gas.

The diffusion process is incomplete at temperatures below 660° C. The residual aluminum, partially diffused oxygen, and other atomic species of the component are observed to grade approximately linearly in composition between the semi-pure aluminum oxide grown layer and the pure component alloy over a thickness related to the ion implantation energy. This composition gradient improves adhesion by gradually modifying the material properties over a relatively large thickness, rather than transitioning the properties at an abrupt interface.

This invention features a process for ion beam treating an alloy consisting primarily of cobalt and chromium for use as an orthopaedic implant component. The component is preferably a femoral hip ball or femoral knee component. The process includes immersing the implant component in an oxygen-containing gas including at least one of oxygen, ozone, water vapor, or hydrogen peroxide, and providing an ion beam consisting primarily of aluminum ions to the immersed component. The partial pressure of oxygen-containing gas is preferably between $1 \times 10^{-5}$ Torr and $1 \times 10^{-3}$ Torr. The aluminum ion beam preferably has an energy of between 20 keV and 400 keV. The aluminum ion beam preferably delivers a total ion dose of between $5 \times 10^{16}$ and $5 \times 10^{18}$ ions/cm$^2$. The oxygen-containing gas is preferably oxygen. The process further includes providing heating to the component either by some indirect heating device, through the energy deposited by the ion beam, or both. The indirect heating device may be an electrical resistance heater or an optical heat lamp. The temperature of the component is preferably between 400° and 660° C. The process may further include simultaneously moving the component relative to the ion beam about two transverse axes during implantation to create a more uniform implanted layer. The ion beam may be provided at an angle to the component.

The object of the process is to grow both a surface layer consisting primarily of aluminum oxide and a subsurface interfacial region in which the composition varies between the aluminum oxide of the surface layer and the cobalt-chromium alloy of the component. The thickness of the grown surface layer may be further enhanced by simultaneously providing a source of atoms or molecules at a flux which nearly equals the flux of sputtered atoms escaping from the component due to the aluminum ion bombardment. This enhanced process permits nearly all of the ion implanted aluminum and grown aluminum oxide to be retained on or in the component, rather than partially being lost due to the concurrent sputtering by the aluminum ion beam. The species of the source of atoms or molecules must not be gaseous at the temperatures indicated. The species is preferably aluminum, although many other species are permitted, because ideally the atoms or molecules are not retained on or within the surface of the component. The purpose of the flux is solely to provide sacrificial atoms or molecules which are then preferentially lost due to the aluminum ion sputtering, rather than sputtering away any of the atoms of either the component, the aluminum ion beam, or the diffused oxygen.

BRIEF DESCRIPTION OF THE DRAWINGS

Other objects, features and advantages will occur to those skilled in the art from the following description of a preferred embodiment and the accompanying drawings in which.

DETAILED DESCRIPTION OF THE PREFERRED EMBODIMENTS

Figure 1:
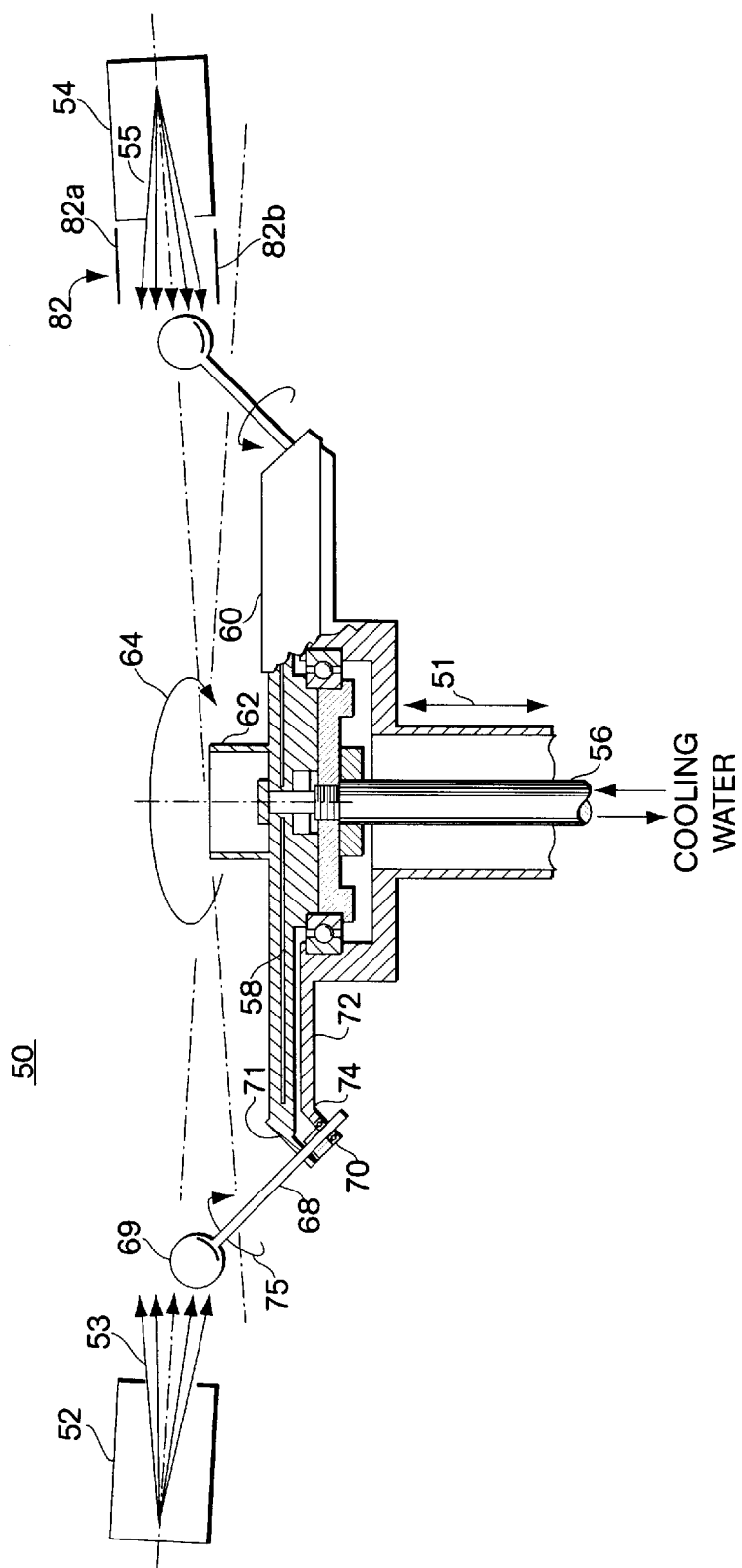
FIG. 1 is a schematic diagram of an ion implantation apparatus for accomplishing the method of this invention.

This invention results from a first realization that a surface layer of an oxide ceramic of aluminum can be created by the simultaneous bombardment of a component by an ion beam consisting of aluminum while the component is immersed in a low pressure gas which includes oxygen atoms. The component may be an alloy composed primarily of cobalt and chromium, such as either case ASTM-F75 alloy or wrought ASTM-F799 alloy. The component may also be a surgical grade of stainless steel. It is further realized that the metal ion most effective in forming aluminum oxide is aluminum. It is further realized that the energy of the bombarding ions should be in the range from 20 to 400 keV and referably at 100 keV. It is further realized that the low pressure oxygen-containing gas may be composed of any one or more of the compounds of pure oxygen, water vapor, ozone, or hydrogen peroxide, with pure oxygen preferred. Other gases, such as nitrogen, may also be present and which do not contribute to the formation of the oxide. It is further realized that the partial pressure of the oxygen-containing gas or gases should be in the range from $5 \times 10^{-6}$ Torr to $1 \times 10^{-3}$ Torr and preferably at $4 \times 10^{-5}$ Torr. It is further realized that the temperature of the component during ion bombardment should be in the range from 400° to 660° C. and preferably at 625° C.

The aluminum ion beam dose may be chosen as desired for the thickness of the grown aluminum oxide layer and should be in the range from $5 \times 10^{16}$ to $5 \times 10^{18}$ atoms/cm$^2$. Preferably, for a flat surface whose normal axis is at an angle of 45° to the direction of the ion beam, the dose is $5 \times 10^{17}$ atoms/cm$^2$ for a 100 keV ion beam. Curved or tilted surfaces at other angles may require other preferred doses, depending on the geometry. The preferred dose is required to make a grown aluminum oxide layer and a graded composition interface zone of sufficient thickness.

Many useful workpieces have steeply curved or tilted surfaces that cannot form an ion implanted buried layer of sufficient thickness to be useful due to the larger value of aluminum ion beam sputtering at higher angles of incidence. Additionally, some of the grown surface layer of aluminum oxide is sputter eroded during the aluminum ion bombardment, thus diminishing the efficiency of growing the surface layer. Both of these difficiencies can be overcome with an alternate embodiment of the process. A source of atoms of aluminum or aluminum oxide is provided with a flux that can be controlled to initially equal that of the sputter erosion of the component. With this special value of the flux, atoms or molecules are being added to the component surface and then sputter eroded essentially immediately. Such a sacrificial flux is not intentionally retained on the surface of the component but only serves to prevent the component itself from being sputter eroded by the aluminum ion beam. Thus, the effect of sputter erosion can be eliminated and the full thickness of the grown aluminum oxide layer retained.

After the desired grown surface layer of aluminum oxide has been formed, the flux from the source of aluminum or aluminum oxide can be increased to begin depositing a coating on the grown surface layer. Assuming that the oxygen containing gas partial pressure is maintained, the deposited aluminum atoms will be mostly converted to aluminum oxide, so a source of aluminum atoms is equivalent to that of aluminum oxide. The advantage of this alternate embodiment is that aluminum oxide is being coated onto a previously grown aluminum oxide without removal from the vacuum chamber, thus permitting a coating process in which a compatible interfacial layer has been pre-formed and the coating performed on a nearly contaminant-free surface.

The flux of aluminum atoms or aluminum oxide molecules may be provided by well-known methods such as high temperature evaporation, sputtering, electron arc discharge, or chemical vapor deposition.

The ion beam current density is defined as the ion beam current divided by the cross-sectional area whose normal axis is parallel to that of the direction of the ion beam. The ion beam current density is typically chosen as high as possible consistent with the ion beam generation equipment used so as to provide a high speed economically viable process. Values of current density greater than 10 microamperes/cm$^2$ are useful in the inventive process. The total ion beam power is defined as the ion beam current times the net accelerating voltage applied to the beam. The total ion beam power divided by the total area swept out by the array of components defines the ion beam power dissipation density. The ion beam power dissipation density plus any auxiliary resistance radiant heating devices is selected to maintain the workpieces at an average temperature between 400° C. to 660° C. during processing.

A spherical workpiece, such as a femoral hip prosthesis, can be ion beam implanted with a graded interface and grown surface layer of aluminum oxide using the apparatus of FIG. 1. Apparatus 50 includes rotatable turntable or fixture 71 fixed to rotatable shaft 56. Below turntable 71 there is a fixed disc 72 having a gear-engaging surface 74 to act as a fixed sun gear. Parts 69 to be coated, for example prosthetic hip balls, are mounted on shafts 68 to which are fixed planetary gears 70, that are engaged with the gear engaging surface of sun gear 72. When shaft 56 is rotated in the direction of arrow 64, balls 69 are caused to rotate around axis 64 as well as shaft axis 75 to simultaneously rotate parts 69 about the two axes. Preferably the angle between axis 64 and axis 75 is acute, and an angle of 49° has been found to result in extremely uniform ion treating of the surfaces of parts 69.

While the parts are rotating, they are exposed to one or more ion beams 55 and 53 that are preferably provided at a slight angle to plane 60 of fixture 50 so that the parts do not shadow each other. For implantation of prosthetic hip ball components, the beam axis is preferably approximately 3° to 10° from plane 60. The important parameter is the prevention of shadowing of one part by another.

Apparatus 50 has been successfully used for uniformly ion-beam coating prosthetic hip balls. Preferably, the balls are spaced as closely as possible together so that ion beam is not wasted. Beams 53 and 55 are typically approximately one inch in diameter and are preferably scanned in relation to the parts being coated by either translating fixture 60 in the direction of arrow 51 or electrostatically deflecting the beams by using deflection mechanism 82, including plates 82a, 82b for applying a voltage gradient across the beam. Preferably, the part-holding fixture is continuously translated up and down a distance approximately equal to the height of the parts being coated to insure that the beams are uniformly scanned across the surfaces being coated.

It is realized that with said apparatus, only a limited area on a spherical component can be ion beam treated with the correct added flux of aluminum atoms or aluminum oxide molecules to exactly compensate for the sputter erosion caused by the aluminum ions. It is further realized that such a limited area consists of those regions on the spherical component subjected to a similar average rate of sputtering as the spherical component is manipulated to present all of its articulating surface to the aluminum ion beam and sacrificial coating deposition source. It is further realized that once sufficient aluminum ion dose has been incorporated into the limited area, that an increase in sacrificial coating flux will then fully enhance the retention of ion implanted aluminum in a second limited area and begin depositing a coating of aluminum oxide over the existing grown surface aluminum oxide in the first limited area.

Therefore, by gradually increasing the added flux of aluminum atoms or aluminum oxide molecules, it is possible to form the desired thickness of the underlayer of grown aluminum oxide across the entire surface area of the component prior to depositing an aluminum oxide overcoating regardless of the complexity of the geometry of the component. If the apparatus of FIG. 1 is employed, the first region to begin adding aluminum oxide coating over the grown surface layer is on the rotational axis of the spherical component.

It is realized that the method of growing a surface layer of aluminum oxide with a sub-surface graded interface layer described for spherical orthopaedic workpieces may also be applied as a general method for other shapes of orthopaedic workpieces, such as femoral knee prostheses. It is further realized that other shapes of orthopaedic workpieces may require a different type of apparatus for manipulating the workpiece to ensure uniform treatment than the type shown in FIG. 1.

EXAMPLE I

Figure 2:
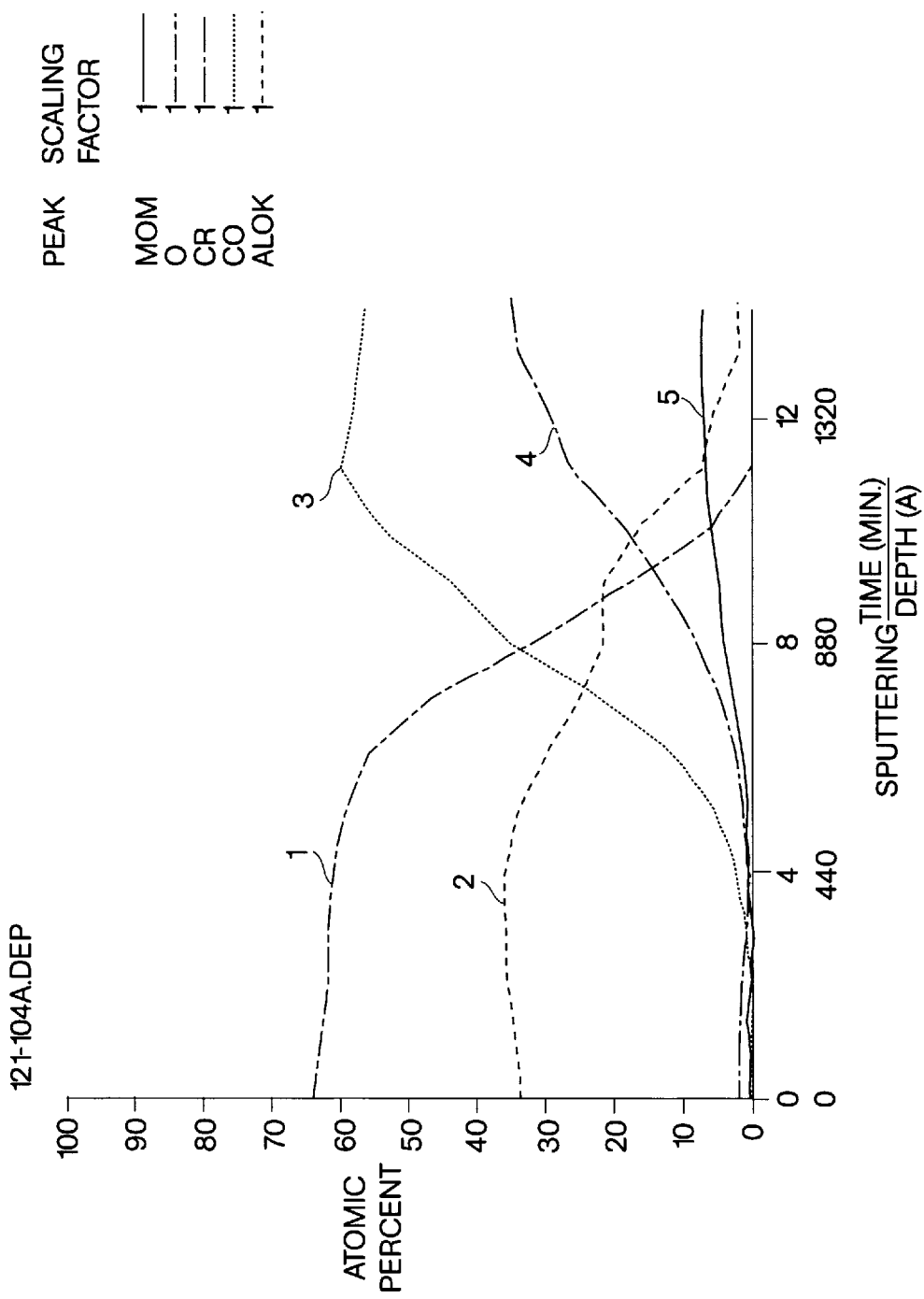
FIG. 2 is a graph of the atomic concentration of the elements found in a specimen of an alloy consisting primarily of cobalt and chromium following ion-induced growth of aluminum oxide by the method of this invention using an aluminum ion beam at 90 keV at an angle of incidence of 45° and a dose of $5 \times 10^{17}$ atoms/cm$^2$ with an oxygen pressure of $2 \times 10^{-5}$ Torr and a component temperature of 630° C. induced by ion bombardment heating.

A flat specimen composed of an alloy of cobalt, chromium, and molybdenum was ion implanted in oxygen gas using the invention with the following process parameters:

Ion Beam Species: $^{27}Al^+$
Ion Beam Energy: 90 keV
Ion Beam Dose: $5 \times 10^{17}$ $Al^+/cm^2$
Oxygen Gas Pressure: $2 \times 10^{-5}$ Torr
Beam Area: 37 $cm^2$
Beam Current: 1.5 mA
Process Time: 15 minutes
Angle of Ion Beam to Surface: 45°
Final Specimen Temperature: 630° C.
Ion Beam Current Density: 25 $\mu A/cm^2$ FIG. 2 shows the resulting Auger Electron Spectroscopy (AES) depth profile of the atomic species near the surface. The various significant elemental species analyzed include oxygen 1, aluminum 2, cobalt 3, chromium 4, and molybdenum 5. There is a layer of approximately 600 Angstroms thickness of nearly pure aluminum oxide, as indicated by the very low percentages of species other than aluminum 2 and oxygen 1. Pure aluminum oxide is expected to exhibit 40 atomic % aluminum and 60 atomic % oxygen, which is within the calibration accuracy of the AES equipment used here. The concentration of oxygen is observed to be relatively constant in the zone corresponding to the grown surface layer and then declining with increasing depth. The sum of the atomic concentrations of oxygen 1+cobalt 3 is observed to be approximately a constant near 60%, indicating that the cobalt atoms have diffused away from the inward diffusing oxygen. This indicates that the oxygen is chemically combined with the remaining aluminum, chromium, and/or molybdenum, but not the cobalt, which is consistent with the known energies of formation for the respective oxides. The AES spectra also indicate the presence of aluminum oxide due to a well-known subtle shift in the shape of the measured electron energy peaks.

Although specific features of the invention are shown in some drawings and not others, this is for convenience only a some feature may be combined with any or all of the other features in accordance with the invention. Other embodiments will occur to those skilled in the art and are within the following claims.

What is claimed is:

1. A process for ion beam treating a metallic orthopaedic implant component comprising:

(a) immersing the implant component in an oxygen-containing gas at a pressure between $5 \times 10^{-6}$ and $1 \times 10^{-3}$ Torr;

(b) applying an ion beam of aluminum to a surface of the immersed component to form an ion implanted surface and a graded interface layer of aluminum oxide at outer portions of the component, wherein the graded interface layer has a concentration of aluminum oxide that varies according to distance from the ion implanted surface of the component and wherein the concentration increases in purity toward the ion-implanted surface of the component; and (c) applying a source to heating to the immersed component using an independent radiant heating source while applying the ion beam in order to cause diffusion of the aluminum and oxygen, thereby facilitating formation of the aluminum oxide.

2. The process of claim 1 in which the immersed component is one of a femoral hip ball and a femoral knee prosthesis.

3. The process of claim 1 in which the immersed component is composed of an alloy consisting of one of cobalt-chrome and stainless steel and titanium.

4. The process of claim 1 in which said oxygen-containing gas is selected from the group consisting of oxygen, ozone, water vapor, and hydrogen peroxide vapor.

5. The process of claim 1, wherein the ion beam has an energy of between 20 keV and 400 keV.

6. The process of claim 1 in which the aluminum ion beam delivers a total ion dose of between $5 \times 10^{16}$ and $5 \times 10^{18}$ ions/$cm^2$ to the immersed component.

7. The process of claim 1, wherein the ion beam has a current density greater than 10 microamperes/$cm^2$.

8. The process of claim 1, wherein the immersed component is maintained at a temperature in the ion beam from 400° to 660° C.

9. The process of claim 1 further comprising moving the component relative to the ion beam while applying the ion beam.

10. The process of claim 1 in which the aluminum oxide graded interface layer is from 50 Å to 500 Å thick.

11. A process for ion beam treating a metallic orthopaedic implant component comprising:

(a) immersing the implant component in an oxygen-containing gas at a pressure between $5 \times 10^{-6}$ and $1 \times 10^{-3}$ Torr;

(b) applying an ion beam of aluminum to a surface of the immersed component to form an ion-implanted surface, and a graded interface layer of aluminum oxide at outer portions of the component, wherein the graded interface layer has a concentration of aluminum oxide that varies according to distance from the ion-implanted surface of the component and wherein the concentration increases in purity toward the ion-implanted surface of the component;

(c) applying a source of heating to the immersed component using an independent radiant heating source while applying the ion beam in order to cause diffusion of the aluminum and oxygen, thereby facilitating formation of the aluminum oxide; and (d) applying a flux of aluminum or aluminum oxide vapor to the immersed component, so that the flux substantially equals a sputtered atoms flux induced by the ion beam of aluminum during formation of the interface.

12. The process of claim 11, in which the immersed component is a femoral hip ball or femoral knee prosthesis.

13. The process of claim 11 in which the immersed component is composed of an alloy consisting essentially of one of cobalt chrome and stainless steel and titanium.

14. The process of claim 11 in which said oxygen-containing gas is selected from the group consisting of oxygen, ozone, water vapor and hydrogen peroxide vapor.

15. The process of claim 11, wherein the ion beam has an energy of between 20 keV and 400 keV.

16. The process of claim 11 in which the aluminum ion beam delivers a total ion dose of between $5\times10^{16}$ and $5\times10^{18}$ ions/cm$^2$ to the immersed component.

17. The process of claim 11, wherein the ion beam has a current density greater than 10 microamperes/cm$^2$.

18. The process of claim 11, wherein the immersed component is maintained at a temperature in the ion beam from 400° to 660° C.

19. The process of claim 11 further comprising moving the component relative to the ion beam while applying the ion beam.

20. The process of claim 11, wherein the implant component is immersed at the pressure of about $4\times10^{-5}$ Torr.

21. The process of claim 11, wherein the flux of aluminum or aluminum oxide is applied by evaporation, sputtering or arc discharge.

22. The process of claim 11 further comprising after formation of the graded interface, increasing a deposition rate per unit area for the aluminum or the aluminum oxide vapor which exceeds the loss rate from the metallic component caused by aluminum ion beam sputtering so that an additional coating of aluminum oxide is formed over the graded interface layer.

23. The process of claim 11 in which the aluminum oxide graded interface layer is from 50 Å to 5000 Å thick.

24. A process for ion beam treating a metallic orthopaedic implant component comprising:
   (a) immersing the implant component in an oxygen containing gas at a pressure between $5\times10^{-6}$ and $1\times10^{-3}$ Torr;
   (b) applying an ion beam of aluminum atoms at an energy between 20 keV and 400 kev and at a current density of at least 10 microamperes/cm$^2$ to a surface of the immersed component to form an ion-implantable surface; and
   (c) applying a source of heating to the immersed component using an independent radiant heating source to obtain a temperature between 400° C. and 660° C. while applying the ion beam, thereby inducing ion assisted diffusion of the implanted aluminum atoms and oxygen atoms of the oxygen-containing gas to provide an aluminum oxide graded interface layer of 50 Å to 5000 Å thick beneath the ion-implanted surface of at least one outer portion of the component and to provide a coincidentally grown aluminum oxide surface layer on the at least one outer portion of the ion-implanted surface of the component, wherein the graded interface layer has a concentration of aluminum oxide that varies according to distance from the ion-implanted surface of the component and wherein the concentration is nearly pure at the ion-implanted surface before the aluminum oxide surface layer is grown.

25. The process of claim 24, wherein the ion beam has a current density of at least 25 microamperes/cm$^2$.

26. The process of claim 25, wherein the ion beam has an energy of about 100 keV.

27. The process of claim 24, further comprising moving the immersed component relative to the ion beam while applying the ion beam.

28. A process for ion beam treating a metallic orthopaedic implant component comprising:
   (a) immersing the implant component in an oxygen-containing gas at a pressure between approximately $5\times10^{-6}$ Torr and approximately $1\times10^{-3}$ Tort;
   (b) applying an ion beam of aluminum to a surface of the immersed component to form an ion-implanted surface, and a graded interface layer of aluminum oxide at outer portions of the component, wherein the graded interface layer has a concentration of aluminum oxide that varies according to distance from the ion-implanted surface of the component and wherein the concentration increases in purity toward the ion-implanted surface of the component;
   (c) applying a source of heating to the immersed component using an independent radiant heating source while applying the ion beam in order to cause diffusion of the aluminum and oxygen, thereby facilitating formation of the aluminum oxide; and
   (d) applying a source of aluminum or aluminum oxide vapor to the immersed component.

29. The process of claim 28, wherein further comprising selecting a deposition rate per unit area for the aluminum or the aluminum oxide vapor which exceeds a loss rate of atoms from the metallic component caused by aluminum ion bean sputtering so as to form an aluminum oxide surface layer after forming the graded interface layer.

30. The process of claim 28, wherein the component is maintained at a temperature of approximately 625° C.

* * * * *